United States Patent
Nelson et al.

(12)

(10) Patent No.: US 6,312,915 B1
(45) Date of Patent: *Nov. 6, 2001

(54) **TICK (*IXODES SCAPULARIS*) VECTOR SALIVA-INDUCED LYME DISEASE SPIROCHETE (*BORRELIA BURGDORFERI*) ANTIGENS AS VACCINE CANDIDATES**

(75) Inventors: David R. Nelson; Thomas N. Mather, both of Wakefield, RI (US); Angelo Scorpio, Columbia, MD (US)

(73) Assignees: The Board of Governors for Higher Education, State of Rhode Island; Providence Plantations, both of Providence, RI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/790,569

(22) Filed: Jan. 29, 1997

Related U.S. Application Data

(62) Division of application No. 08/548,497, filed on Oct. 26, 1995, now abandoned.

(51) Int. Cl.[7] .................... G01N 33/53; G01N 33/569; G01N 33/554; G01N 33/537
(52) U.S. Cl. .................... 435/7.1; 435/7.22; 435/7.32; 435/7.92; 435/34; 435/41; 436/506
(58) Field of Search .................... 435/7.1, 7.32, 435/7.92, 34, 41, 7.22; 530/350, 820, 825; 424/130.1, 178.1, 184.1, 234.1; 436/506

(56) References Cited

U.S. PATENT DOCUMENTS 5,283,259 * 2/1994 Mather .

FOREIGN PATENT DOCUMENTS

9470373 * 8/1994 (AU) .

OTHER PUBLICATIONS

Ewing et al. (1994) J. Clin. Microbiol. vol. 32 (3), 755–758.*
Govenflot et al. (1990) Infect and Immunit. vol. 58(12), 4076–4082.*
Megnarelli et al. (Oct. 1995) vol. 33(10), 2710–2714.*

* cited by examiner

*Primary Examiner*—Albert Navarro
(74) *Attorney, Agent, or Firm*—Samuels, Gauthier & Stevens

(57) ABSTRACT

The invention relates to a method by which new antigens from vector-borne pathogens may be discovered and analyzed by incubating the viable pathogens in the saliva of their vector host. Three such antigens, proteins with the approximate molecular weights of 19, 22 and 24 kDa, have been discovered and analyzed from a strain of *B. burgdorferi* T-15. The proteins provide a route for the development of immunodiagnostics for Lyme disease and related disorders. The proteins and related amino acids and DNA sequences may also be used for the immunization, for the detection of *B. burgdorfei* in human or body fluids, and also for the generation of specific antibodies for use in diagnosis, epidemiology, prevention of and treatment of Lyme disease.

9 Claims, 7 Drawing Sheets

Figure 1A:
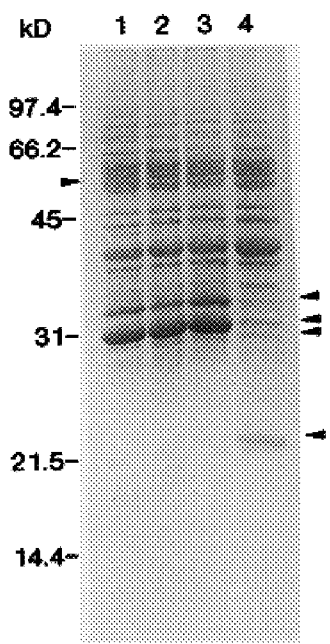

TICK (IXODES SCAPULARIS) VECTOR SALIVA-INDUCED LYME DISEASE SPIROCHETE (BORRELIA BURGDORFERI) ANTIGENS AS VACCINE CANDIDATES

This is a divisional of application(s) Ser. No. 08/548,497 filed on Oct. 26, 1995, now abandoned.

FIELD OF THE INVENTION

The present invention relates to the use of the saliva of a member of the family Ixodidae to induce the expression of proteins by *Borrelia burgdorferi*. Novel tick saliva-induced *B. burgdorferi* proteins can be used for the potential development of a vaccine against Lyme disease and for improved diagnostic kits for the detection of Lyme disease.

BACKGROUND OF THE INVENTION

*Borrelia burgdorferi*, a spirochete, is the causative agent of Lyme disease. It is a vector borne pathogen, transmitted by ticks of the *Ixodes scapularis* and *Ixodes pacificus* complexes in the United States. Burgdorfer W., *B. burgdorferi*: Its Relationships to Tick Vectors, In Staken (ed): Lyme Borreliosis, II, Zbl Bakt Supplement 18, Stuttgart-New York, Gustav Fischer, 8–13, 1989. Infection with *B. burgdorferi* is the most common tick-borne infectious disease in the United States. In endemic areas, between 30 and 90% of Ixodes ticks are infected with this organism.

The illness caused by *B. burgdorferi* is a multisystem infection that affects the skin, central nervous system, peripheral nerves, the heart and the joints, with nerve and joint involvement being the most common. Steere, A. C., S. E. Malawista, J. A. Hardin, S. Ruddy, W. Askenase, and W. A. Andiman, Erythema Chronicum Migrans and Lyme Arthritis: the Enlarging Spectrum, Ann Intern Med. 86:685–698, 1977a. The dissemination of spirochetes over time from the site of infection has been documented in a mouse model. Barthold, S. W., D. H. Persing, A. L. Armstrong, and R. A. Peeples, Kinetics of *B. burgdorferi* Dissemination and Evolution of Disease after Intradermal Inoculation of Mice, AM J. Pathol, 139:263–273, 1991. In these experiments it was shown that the spirochetes were multifocal in distribution with a predilection for collagenous connective tissue of joints, heart, arteries, nerves, muscles, skin and other tissues. In humans, nerve, joint and heart involvement is usually manifested when the disease reaches a chronic state. The pathogensis to a chronic state of nerve involvement, termed neuroborreliosis, is unclear, but may be due to a direct effect of the spirochetes at the site of infection, the host response to *B. burgdorferi*, or the host response to tissue antigens that may mimic those of *Borrelia burgdorferi*. Fikrig, E., R. Berland, M. Chen, S. Williams, L. H. Signal, and R. A. Flavell, Serological Response to *B. burgdorferi* Flagellin Demonstrates an Epitope Common to a Neuroblastoma Cell Line, Proc. Natl. Acad. Sci. 90:183–187, 1993. For example, spirochetes can be detected in the cerebrospinal fluid of patients with neuroborreliosis with a corresponding high level of antigen specific T-cells which suggests that a local immune response may be involved in the disease. However, the presence of spirochetes has yet to be demonstrated in biopsy specimens of affected nerve tissue suggesting that clinical manifestations may be due to some type of molecular mimicry. Indeed, it has been shown that antibodies reactive to a certain epitope of the *B. burgdorferi* flagellin molecule cross react with a neuroblastoma cell line. Fikrig, E., R. Berland, , M. Chen, S. Williams, L. H. Sigal , and R. A. Flavell, Serological Response to *B. burgdorferi* Flagellin Demonstrates an Epitope Common to a Neuroblastoma Cell Line, Proc. Natl. Acad. Sci. 90:183–187, 1993. Development of arthritic symptoms is similarly complex. Patients who develop arthritis usually show involvement of the knee joint with an increase of polymorphonuclear granulocytes in the synovial fluid. Steere, A. C., S. E. Malawista, and D. R. Snydman, Lyme Arthritis: An Epidemic of oligoarticular Arthritis in Children and Adults in Three Connecticut Communities, Arthritis Rheum. 20:7–17, 1977. It has been hypothesized that spirochetes trigger a local immune response with autoreactive features in the joint, symptoms which may continue after the organisms no larger are viable. Girouard, L., D. C. Laux, S. Jindal, and D. R. Nelson, Immune Recognition of Human Hsp60 by Lyme Disease Patient Sra, Microb. Pathog. 14:287–297, 1993; and Steere, A. C., J. Feld, and R. Winchester, Association of Chronic Lyme Arthritis with Increased Frequencies of DR4 and 3, Arthritis Rheum. 31:98 (Abstract), 1988. As with nerve biopsies, culturing of spirochetes from synovial fluid of the joints is exceedingly difficult, being reported only twice, and direct observation is also rare. These phenomena are especially true as the disease progresses. Recent advances in the ability to detect small amounts of DNA using polymerase chain reaction (PCR) has led to conflicting results regarding the presence of spirochetes in the joint. Nocton, J. J., F. Dressler, B. J. Rutledge, P. N. Rys, D. H. Persing, and A. C. Steere, Detection of *B. burgdorferi* DNA by Polymerase Chain Reaction in Synovial Fluid in Lyme Arthritis, N. Engl. J. Med. (In press); and Malawista, S. E., T. L. Moore, D. E. Dodge, T. J. White, R. T. Schoen, and D. H. Persing, Failure of Multitarget Detection of *Borrelia burgdorferi*-Associated DNA Sequences in Synovial Fluids of Patients with Juvenile Rheumatoid Arthritis: A Cautionary Note, Arthritis Rheum. 35:246–247, 1992. Thus, as with neuroborreliosis, there appear to be two possibilities: septic arthritis with live organisms in the joint, and reactive arthritis where a microbial antigen at a remote site stimulates an immune response involving either antibodies or cytotoxic mononuclear cells that cross-react with a compartment of host tissue.

The humoral response to *B. burgdorferi* has been well documented. There is a potent response to the 41 kDa flagellar protein early during the course of infection followed by an antibody response to various other proteins, notably Hsp60, Hsp70, a 66 kDa protein and other lower molecular weight proteins. Chronic infection generally results in development of an antibody response to the outer surface lipoproteins A and B (OspA and OspB). Barbour, A. G., W. Burgdorfer, E. Grunwaldt, and A. C. Steere, Antibodies of Patient with Lyme Disease to Components of the Ixodes Dammini Spirochete, J. Clin. Invest. 72:504–510, 1983. These and other outer surface proteins have been given a great deal of attention because of their potential as vaccine candidates and because of their possible virulence functions. Antibodies against OspA have been shown to be protective against Lyme disease—mice immunized with recombinant OspA are resistant to infection with *Borrelia burgdorferi*. Fikrig, E., S. W. Barthold, F. S. Kantor, and R. A. Flavell, Protection of Mice Against the Lyme Disease Agent by Immunization with Recombinant OspA, Science. 250:553–556, 1990, and sera containing antibodies against OspA has been shown to exhibit borreliacidal activity independent of complement. Callister, S. M., R. F. Schell, K. L. Case, S. D. Lovrich, and S. P. Day, Characterization of the Borreliacidal Antibody Response to *B. burgdorferi* in Humans: A Serodiagnostic Test, J. Infect. Dis. 167:158–164, 1992. Similarly, a bactericidal antibody directed against OspB has also been reported. Sadziene, A., M. Jonsson, S. Bergstrom, R. K. Bright, R. C. Kennedy, and A. G. Barbour, A Bactericidal Antibody to *B. burgdorferi* is Directed Against a Variable Region of the OspB Protein, Infect. Immun. 62:2037–2045, 1994.

Despite the appearance of a humoral immune response to OspA and OspB during the course of infection and the proven effectiveness of antibodies against these proteins in killing *B. burgdorferi* and preventing infection, disease symptoms generally do not resolve without treatment. Vaccination of mice after infection with *B. burgdorferi* has been shown to partially clear spirochetes from the bloodstream and also to reduce the severity of disease symptoms, however, it did not eliminate them from other tissues, nor did it alter the course of joint and heart involvement. Fikrig, E., S. W. Barthold, and R. A. Flavell, OspA Vaccination of Mice with Established *B. burgdorferi* Infection Alters Disease but not Infection, Infect. Immun. 61:2553–2557, 1993. This implies that *B. burgdorferi* may be able to occupy immunologically priveledged sites where it is not accessible to antibodies or that it is able to evade immune response by altering its outer surface. OspA and OspB are the best characterized of the *B. burgdorferi* antigens and have been implicated as virulence factors. For example, it has been shown that a monoclonal antibody to OspA inhibits association of *B. burgdorferi* with human endothelial cells. Comstock, L. E., E. Fikrig, R. J. Shoberg, R. A. Flavell and D. Thomas, A Monoclonal antibody to OspA Inhibits Association of *B. burgdorferi* with Human Endothelial Cells, Infect. Immun. *61:423–431*, and loss of a functional OspB protein results in a dramatic decrease in pathogenicity of *B. burgdorferi*. Schwan, T. G., W. Burgdorfer, and C. F. Garon, Changes in Infectivity and Plasmid Profile of the Lyme Disease Spirochete, *B. burgdorferi*, as a Result of In Vitro Cultivation, Infect. Immun., 56:1831–1836, 1988; and Sadziene, A., A. G. Barbour, P. A. Rosa, and D. D. Thomas, An OspB Mutant of *B. burgdorferi* has Reduced Invasiveness in Vitro and Reduced Infectivity in Vivo, Infect. Immun. 61:3590–596, 1993. Since the discovery of OspA and OspB, several other surface lipoproteins have been identified that are immunologically recognized and may also play an important role in disease pathogenicity. These have been named accordingly OspC,D,E, and F, and are being investigated as possible vaccine candidates.

The Borrelia genome is unique among the pathogenic spirochetes in that it contains both linear and circular plasmids accounting for approximately 150-kb. Barbour, A. G., Plasmid Analysis of *B. burgdorferi*, the Lyme Disease Agent, J. Clin. Microbiol. 26:475–478, 1988. Considering that the size of the genome in *B. burgdorferi* has been measured at approximately 950-kb, plasmid DNA accounts for a large fraction of the total DNA. Ferdows, M. S., and A. G. Barbour, Megabase-Sized Linear DNA in the Bacterium *B. burgdorferi*, the Lyme Disease Agent, Proc. Natl. Acad. Sci. 86:5969–5973, 1989. In *Borrelia hermsii*, a relapsing fever species, the genes for major outer membrane proteins are also arrayed on linear plasmids, Ferdows and Barbour, supra. This unique feature can result in the loss of plasmids during growth which is especially true during cultivation in growth media, Schwan et al. supra. One advantage a loss of plasmids may confer on the spirochete is the ability to evade the immune response. For example, antibodies directed against OspA will not affect a spirochete that has lost the plasmid encoding the OspA protein. A disadvantage is that the spirochete will suffer a decrease of virulence capabilities. All of the outer surface lipoproteins discovered thus far are located on plasmids. OspA and OspB are co-transcribed on a 49-kb linear plasmid, Bergstrom, S., V. G. bundoc, and A. G. Barbour, Molecular Analysis of Linear Plasmid-Encoded Major Surface Proteins, OspA and OspB, of Lyme Disease Spirochete *B. burgdorferi*, Mol. Microbiol. 3:479–486, 1989, OspD is located on a 38-kb plasmid, Norris, S. J., C. J. Carter, J. K. Howell, and A. G. Barbour, Low-Passage-Associated Proteins of *B. burgdorferi* B31: Characterization and Molecular Cloning of OspD, a Surface-Exposed, Plasmid-Encoded Lipoprotein, Infect. Immun. 60:4662–4672, 1992, OspC on a 26-kb plasmid, Fuchs, R., S. Jauris, F. Lottspeich, V. Preac-Mursic, B. Wilske, and E. Soutschek, Molecular Analysis and Expression of a Borrelia Gene Encoding a 22 kDa Protein (pC) in *Escherichia coli*, Mol. Microbiol. 6:503–509, 1992, and OspE and OspF are co-transcribed on a 45-kb linear plasmis, Lam, T., T. K. Nguyen, R. R. Montgomery. F. S. Kantor, E. Fikrig, and R. A. Flavell, Outer Surface Proteins E and F of *B. burgdoferi*, The Agent of Lyme Disease, Infect. Immun. 62:290–298, 1994.

*B. burgdorferi* has a cell organization similar to that of other spirochetes. The bacterium has an inner or cytoplasmic membrane that is surrounded by periplasmic flagella. The flagella wraps around the cytoplasmic cylinder making the cell motile by a corkscrew motion. These structures are covered by a peptidoglycan cell wall and an outer membrane. Although it stains as a gram negative bacterium, it is different from other gram negative bacteria in that the peptidoglycan layer is attached to the cytoplasmic membrane instead of the outer membrane. As such, the outer membrane of *B. burgdorferi* is quite fragile, often releasing from the cell as small vacuoles or "blebs". Various attempts have been made to study the various components of the cell structure to better understand its mechanisms of pathogenesis. These methods include detergent treatment of cells to separate inner and outer membrane components. Brusca, J. S., A. W. McDowall, M. V. Norgard, and J. D. Radolf, Localization of Outer Surface Proteins A and B in Both the Outer Membrane and Intracellular Compartments of *B. burgdorferi*, J. Bacteriol. 173:8004–8008, 1994; freeze-fracture electron microscopy to visualize membrane and membrane bound proteins, Radolf, J. D., K. W. Bourell, D. R. Akins, J. S. Rusca, and M. V. Norgard, Analysis of *B. burgdorferi* Membrane Architecture by Freeze-Fracture Electron Microscopy, J. Bacteriol. 176:21–31, 1994, and isopycnic centrifugation to separate inner and outer membrane proteins without the use of detergents, Bledsoe, H. A., J. A. Carroll, T. R. Welchel, M. A. Farmer, D. W. Dorward, and F. C. Gherardini, Isolation and Partial Characterization of *B. burgdorferi* Inner and Outer Membranes by Using Isopycnic Centrifugation, J. Bacteriol. 176:7447–7455, 1994.

A recent report has shown that spirochetes can be observed in the midgut, hemolymph, and saliva of Lyme Disease ticks by direct immunofluorescence assays at various stages of the feeding process. Using this technique, transmission of *B. burgdorferi* from a tick to a host was shown to be multi-step process that probably results in delivery of the spirochetes into the host via the salivary glands. Ribiero, J. M. C., Mather, T. N., Piesman, J., and Spielman, A., Dissemination and Salivary of Lyme Disease Spirochetes in Vector Ticks (Acari:Ixodidae), J. Med. Entomol, 24:201–205, 1987.

BRIEF SUMMARY OF THE INVENTION

While other modes of transfer have been proposed, the present disclosure of the invention supports the concept of salivary delivery by demonstrating that *B. burgdorferi* can be grown in BSKII from a saliva inoculum.

Prior to engorgement, *B. burgdorferi* resides in the tick midgut. Feeding of the tick triggers the spirochete's dissemination into the surrounding hemolymph and eventually into the salivary glands. The invention embodies the discovery of the effect of tick saliva on newly discovered protein(s) expressed in *B. burgdorferi*. It is believed that the saliva has an appreciable effect on protein synthesis and that this effect is partly responsible for successful transmission to a host.

Saliva from *Ixodes scapularis* has been shown to contain several factors that regulate the host immune response, Ribiero, J. M. C., Mather, T. N., Piesman, J., and Spielman, A., Dissemination and Salivary Delivery of Lyme Disease Spirochetes in Vector Ticks (Acari:Ixodidae), J. Med. Entomol, 24:201–205, 1987. These factors which include anti-inflammatory and anti-complement compounds aid the tick against host defenses during feeding and probably benefit the spirochete as well.

The invention is broadly directed to the discovery that the saliva of blood sucking arthropods (including but not limited to ticks, mosquitos and other biting flies) contains substances which cause the expression of proteins which significantly enhance the transmission of vector borne pathogens from the arthropod to the host. The pathogens can also comprise those identified in the families Borreliae, Rickettsiae and Ehrlichiae. The pathogens can comprise protozoan parasites classified as piroplasms for example Babesia and Theileria.

The present invention in a preferred embodiment is directed to the culturing of *B. burgdorferi* in the saliva of the tick *I. scapularis* and the identification of the proteins expressed in said culture. The invention is also directed to the identification and purification of newly discovered proteins expressed by *B. burgdorferi*. The expression of these proteins is considerably enhanced in the saliva of the *Ixodes scapularis* tick.

Based on the discovery of saliva-induced proteins, the present invention can address problems associated with the preparation and use of *B. burgdorferi*-specific antigens, particularly those antigens associated with virulence and which are useful for developing detection and diagnostic methods for Lyme disease. The invention can result in the identification of such antigens, as well as the identification and isolation of *B. burgdorferi* nucleic acid sequences that encode *B. burgdorferi* antigens or antigenic polypeptides derived therefrom. These sequences are useful for preparing expression vectors for transforming host cells to produce recombinant antigenic polypeptides. It is further proposed that these antigens will be useful as vaccines or immunodiagnostic agents for *B. burgdorferi* associated diseases such as Lyme disease in particular.

The nucleic acid segments can encode antigenic amino acid sequences associated with virulent *B. burgdorferi*. These sequences are important for their ability to selectively hybridize with complementary stretches of *B. burgdorferi* gene segments.

In clinical diagnostic embodiments, nucleic acid segments of the present invention may be used in combination with an appropriate means, such as a label, to determine hybridization with DNA of a pathogenic organism. Typical methods of detection might utilize, for example, radioactive species, enzyme-active or other marker ligands such as avidin/biotin, which are detectable directly or indirectly. In preferred diagnostic embodiments, an enzyme tag such as alkaline phosphatase or peroxidase can be employed rather than radioactive or other reagents that may have undesirable environmental effects.

Hybridizable DNA segments may include any of a number of segments of the disclosed DNA.

In embodiments relating to antigen production, DNA segments that encode an antigenic polypeptide are derived from the amino acid sequence of an antigen of *B. burgdorferi*. Particularly preferred for such an application is the saliva-induced 19, 22 or 24 kDa *B. burgdorferi* antigen.

While the 19, 22 or 24 kDa saliva-induced *B. burgdorferi* proteins disclosed herein are based on a specific isolate which will result in specific amino acid sequences, it is nonetheless contemplated that the amino acid sequence will be found to vary from isolate to isolate. Moreover, it is quite clear that changes may be made in the underlying amino acid sequence through, for example, site-directed mutagenesis of the DNA coding sequence, in a way that will not negate its antigenic capability.

The invention also relates to at least partially purified *B. burgdorferi* proteins or polypeptides which are capable of producing an in vivo immunogenic response when challenged with *B. burgdorferi*.

In other aspects, the invention concerns recombinant vectors such as bacterial plasmids, phage or viruses which comprise DNA segments in accordance with the invention, for use in replicating such sequences or even for the expression of encoded antigenic peptides or proteins. Vectors or plasmids may be used to transform a selected host cell. In preparing a suitable vector for transforming a cell desired DNA segments from any of several *B. burgdorferi* sources may be used including genomic fragments, DNA or synthetic DNA.

Expression vectors may be constructed to include any of the DNA segments which encode the disclosed proteins. Such DNA might encode an antigenic protein specific for virulent strains of *B. burgdorferi* or even hybridization probes for detecting *B. burgdorferi* nucleic acids in samples. Depending on the antigenic protein desired, longer or shorter DNA segments could be used. Epitopic regions of the proteins expressed or encoded by the DNA could be included as relatively short segments of DNA. A wide variety of expression vectors is possible including, for example, DNA segments encoding reporter gene products useful for identification of heterologous gene products and/or resistance genes such as antibiotic resistance genes which may be useful in identifying transformed cell.

Recombinant vectors are particularly preferred for transforming bacterial host cells. Accordingly, a method for preparing transformed bacterial host cells that includes generally the steps of selecting a suitable bacterial host cell, preparing a vector containing a desired DNA segment and transforming the selected bacterial host cell will be used. Several types of bacterial host cells may be employed, including *Borrelia burgdorferi, E. coli, B. subtilus* and the like as well as prokaryotic host cells.

Transformed cells may be selected using various techniques, including screening by differential hybridization, identification of fused reporter gene products, resistance markers, anti-antigen antibodies and the like. After identification of an appropriate clone, it may be selected and cultivated under conditions appropriate to the circumstances, as for example, conditions favoring expression or, when DNA is desired, replication conditions.

Another aspect of the invention involves the preparation of antibodies and vaccines from the 19, 22 or 24 kDa saliva-induced proteins or epitopic regions of those proteins (alone or in combination) encoded by the DNA. The invention thus relates to one or more antibodies, monoclonal or polyclonal, that may be generated in response to the 19, 22 or 24 kDa *B. burgdorferi* saliva-induced protein or its epitopes. It is expected that the sensitivity and specificity of antibody response to these antigens and their epitopes will be superior to the response that has been obtained from other *B. burgdorferi* antigens that are not associated with virulence.

In both immunodiagnostics and vaccine preparation, it is often possible and indeed more practical to prepare antigens from segments of a known immunogenic protein or polypeptide. Certain epitopic regions may be used to produce responses similar to those produced by the entire antigenic polypeptide. Potential antigenic or immunogenic regions may be identified by any of a number of approaches.

It is contemplated that the antigens and immunogens of the invention will be useful in providing the basis for one or more assays to detect antibodies against *B. burgdorferi*. Previous assays have used whole *B. burgdorferi* as the antigen. Sera from normal individuals not exposed to *B. burgdorferi* often contain antibodies that react with *B. burgdorferi* antigens, in particular antigens that have epitopes in common with other bacteria. It is necessary to adjust assay conditions or the diagnostic threshold or reactivity to avoid false positive reactions due to these cross-reactive antibodies in normal sera. These adjustments may in turn decrease the sensitivity of the assay and lead to false negative reactions, particularly in the early stages of *B. burgdorferi* infection. Assays using the disclosed 19, 22 or 24 kDa saliva-induced proteins or antigenic polypeptides thereof, are expected to give superior results both in sensitivity and selectivity when compared to assays that use whole *B. burgdorferi* or even purified flagella in either an indirect ELISA or an antibody capture ELISA format.

It is further anticipated that a recombinant-derived from any of 19, 22 or 24 kDa saliva-induced *B. burgdorferi* proteins will be particularly preferred for detection *B. burgdorferi* infections.

Preferred immunoassays are contemplated as including various types of enzyme linked immunoassays (ELISAS), immunoblot techniques, and the like, known in the art. However, it will be readily appreciated that utility is not limited to such assays, and useful embodiments include RIAs and other nonenzyme linked antibody binding assays or procedures.

Yet another aspect of the invention is a method of detecting *B. burgdorferi* nucleic acid in a sample. The presence of *B. burgdorferi* nucleic acid in the sample may be indicated by the presence of the polypeptide products which it encodes. The method therefore includes detecting the presence of at least a portion of any of the polypeptides herein disclosed. Suitable detection methods include, for example, immunodetection reagents, PCR amplification, and hybridization.

Methods of diagnosing Lyme disease are also included in the invention. In one embodiment, an antibody-based method includes obtaining a sample from a patient suspected of having Lyme disease, exposing that sample to one or more epitopes of the *B. burgdorferi* protein which is encoded by the DNA disclosed and finally determining a reactivity of the antibody with one or more epitopes of a *B. burgdorferi* protein that may be in the sample. The reactivity measured is indicative of the presence of Lyme disease.

Likewise, reactive epitopes of the 19, 22 or 24 kDa saliva-induced proteins are contemplated as useful either an antigens in an ELISA assay or to inhibit the reaction of antibodies toward intact 30 kDa protein bound to a well.

Epitopic peptides could be generated by recombinant DNA techniques previously disclosed or by synthesis of peptides from individual amino acids. In either case, reaction with a given peptide would indicate presence of antibodies directed against more epitopes. In addition to its diagnostic potential, this method is seen as being particularly effective in characterizing monoclonal antibodies against the 19, 22 or 24 kDa saliva-induced proteins and other virulence associated proteins.

The invention also relates to monoclonal antibodies directed toward one or more epitopes of the antigenic protein encoded by the DNA. In preferred embodiments, such antibodies lack cross reactivity with antigens found in other bacteria. Monoclonal antibodies against the proteins and other virulence associated proteins are generated by using hybridomas which can be produced and screened. Proteins produced by *B. burgdorferi* or recombinant DNA vectors and purified by two-dimensional electrophoresis or other methods could be used for immunization of animal models such as BALB/C mice. Selection of reactive clones is carried out with a typical ELISA assay using the immunizing protein as antigen. Western immunoblots could also be used in a screening or confirmatory assay.

Such monoclonal antibodies are envisioned as useful in several respects including (1) detection of *B. burgdorferi* in tissues or body fluids by immunofluorescence, enzyme immunoreactions, such as immunoperoxidase staining of tissue sections, avidin-biotin indicator enzyme immunoassays, or other techniques, (2) rapid screening of *B. burgdorferi* strains and clones as well as *E. coli* recombinants for expression of the protein, (3) determination of structural locations of proteins by immuno electron microscopy, (4) identification of reactive epitopes using a peptide library, (5) demonstration of bacteriocidal activity in vitro in combination with compliment and selection of protein deficient mutants, (6) assessment of immunoprotective activity by passive immunization, (7) used to study host cell interactions by inhibition of adherence or penetration or by enhancement or engulfment and killing by phagocytic cells, and (8) possible use for epidemiological studies particularly in studying variation of *B. burgdorferi* strains in expression of proteins or protein sequences.

In further aspects, the present invention concerns a kit of the detection of *B. burgdorferi* antigens. Alternatively, the kit includes an antibody reactive with any of the saliva-induced proteins 19, 22 or 24 kDa or a protein or peptide which includes an epitope thereof, together with means for detecting a specific immunoreaction between an antibody and its corresponding antigen. Examples of suitable means include labels attached directly to the antigen or antibody, a secondary antibody having specificity for human Ig, or protein A or protein G. Alternatively, avidin-biotin mediated *Staphylococcus aureus* binding could be used. For example, the monoclonal antibody may be biotinylated so as to react with avidin complexed with an enzyme or fluorescent compound.

A particular kit embodiment of the invention concerns detection of antibodies against the described *B. burgdorferi* 19, 22 or 24 kDa saliva-induced antigen, epitopes thereof as represented by portions of the amino acid sequences, or closely related proteins or peptides, such as epitopes associated with other virulence-associated proteins detected by comparison of low-passage, virulent and high-passage, avirulent strains of *B. burgdorferi*. The antigen for the kit(s) consists of the *B. burgdorferi* 19, 22 or 24 kDa saliva-induced protein or portions thereof produced by a recombinant DNA vector in *E. coli* or another bacterial or nonbacterial host. Alternatively, the antigen may be purified directly from B. burgdorferi or manufactured as a synthetic peptide. Samples for the assays may be body fluids or other tissue samples from humans or animals. The presence of reactive antibodies in the samples may be demonstrated by antibody binding to antigen followed by detection of the antibody-antigen complex by any of a number of methods.

In still further embodiments, the invention contemplates a kit for the detection of B. burgdorferi nucleic acids in the sample, wherein the kit includes one or more nucleic acid probes specific for the 19, 22 or 24 kDa saliva-inducible genes, together with means for detecting a specific hybridization between such a probe and *B. burgdorferi* nucleic acid, such as an associated label.

It is believed that saliva may regulate the protein expression of a pathogen as a result of its nutritional content. The saliva of the tick probably contains a paucity of nutrients. For example, the protein concentration as measured by the Bio-Rad assay, is about 50 μg/ml in *I. scapularis*. Though the concentration of glucose and other metabolites has not been directly measured, they too are probably relatively low. The passage of the spirochetes into the host via the saliva may initiate a stress response by the spirochetes to a low nutrient concentration or some other factor(s) in the saliva. It is reasonable to assume that *B. burgdorferi* has an efficient and highly regulated starvation response, for while it is a fastidious bacterium (it is grown in a complex laboratory medium), in nature it must be able to cope with long periods of relatively low nutrient conditions where little or no growth occurs while residing in the midgut of a tick. As the saliva appears to be the last environment seen by the spirochetes prior to entry into the host, the protein expression response to incubation in saliva by *B. burgdorferi* is of interest.

Because *B. burgdorferi* probably spends a significant amount of time exposed to tick saliva during transmission, the effect of the saliva on protein expression in *B. burgdorferi* was investigated and is described hereinafter based on the hypothesis that proteins preferentially expressed during incubation in saliva, in particular, membrane-bound proteins, are important for successful transmission and/or virulence. It is also hypothesized that outer surface proteins whose expression is elevated in saliva are good candidates for vaccine development.

BRIEF DESCRIPTION OF THE DRAWINGS

FIG. 1*a* is a coomassie stain of *B. burgdorferi* isolates. Each isolate was grown in 15 ml BSKII. The cells were washed in PBS, resuspended in sample buffer, and boiled for 5 minutes. Lysates were then examined by SDS-PAGE and coomassie blue staining. Lane 1—Isolate W7. 2—I3. 3—I2. 4—B31;

FIG. 1*b* is a fluorogram of [$^{35}$S]methionine labeled *B. burgdorferi* isolates. Cells were labeled at either 33° C. or 41° C. for 1 h. Equal counts per lane were loaded and resolved by SDS-PAGE and fluorography. Lane 1—B31. 2—I4. 3—W2;

FIG. 2*a* is a 2-dimensional Western blot of *B. burgdorferi* proteins with antibodies against Hsp60 (LAλ8), Hsp70 (LA3), OspA (H5332), OspB (H6331), and LA7 (pLA7). Cells labeled with [$^{35}$S]methionine in RPMI were subjected to 2-dimensional gel electrophoresis and transferred to nitrocellulose. Proteins were all probed simultaneously on a single nitrocellulose sheet (A);

FIG. 2*b* is an autoradiogram resulting form exposure of the 2-dimensional Western blot to an piece of X-ray film. Proteins corresponding to the antibodies used are indicated;

FIGS. 3*a* and 3*b* are 2-dimensional gel electrophoreses of [$^{35}$S]methionine labeled proteins. *B. burgdorferi* was labeled in either RPMI or *Ixodes scapularis* saliva for 20 h at 33° C. in a candle jar. The labeled cells were then examined by 2-dimensional electrophoresis in pH 5–7 gels followed by fluorography. Proteins whose expression is regulated by saliva are indicated. A) Hsp70 B) Hsp60 C) 66 kDa protein (p66) D) Flagellin e) 24 kDa protein (p24) F) 22 kDa protein (p22) G) pLA7 H) 19 kDa protein (p19);

FIGS. 4*a*, 4*b* and 4*c* are 2-dimensional gel electrophoresis of [35S]methionine labeled proteins. *B. burgdorferi* was labeled in either A) RPMI, B) *Ixodes scapularis* saliva, or C) *Ixodes scapularis* midgut extract or 20 h at 33° C. in a candle jar. The labeled proteins were then examined by 2-dimensional electrophoresis in pH 3–10 gels followed by fluorography. Proteins whose expression is regulated by saliva are indicated. A) Hsp70 B) Hsp60 C) 66 kDa protein (p66) D) Flagellin E) OspA F) 24 kDa protein (p24) G) 22 kDa protein (p22) H)plA7 I) 19 kDa protein (p19);

FIG. 5 is a bar graph showing relative levels of saliva-regulated proteins synthesized by *B. burgdorferi* during incubation in either RPMI, *Ixodes scapularis* saliva or *Ixodes scapularis* midgut extract;

FIGS. 6*a* and 6*b* are surface proteolysis of *B. burgdorferi* proteins. Cells were treated with proteinase K as described. A) Fluorogram of proteins from cells labeled with [$^{35}$S] methionine in *Ixodes scapularis* saliva prior to surface proteoysis. B) Coomassie strain of whole cells proteins from *B. burgdorferi;*

FIG. 7 is subcellular fractionation of *B. burgdorferi* proteins labeled with [$35_S$]methionine. *B. burgdorferi* was grown at 33° C. and radioactively labelled in either RPMI (R) or *Ixodes scapularis* saliva (S). Following labelling, the cells were fractionated into membrane Triton X-100 insoluble (C), membrane Triton X-100 soluble (D), and non-membrane soluble (E) proteins. Whole membrane (A) and secreted proteins (B) were also collected. Proteins were resolved by SDS-PAGE and examined by fluorography. Saliva-regulated proteins are indicated.

DESCRIPTION OF THE PREFERRED EMBODIMENTS

The midgut of the tick is a major storage organ for the slow release of nutrients between blood meals. Stores of glycogen, lipids, and proteins make the gut an ideal habitat for both intracellular and intraluminal prokaryotes. The amount of nutrients available, however, is relatively low and as such the non-engorged tick gut probably represents a non-growth state for the spirochete. As indicated, it is the site of residence for *B. burgdorferi* prior to transmission to a host. In the hemocoel of the midgut, the spirochetes adhere to the gut epithelial cells. Gut penetration occurs during active nutrient transport and extensive reorganization of the epithelial cell membranes. At this point, the spirochetes are exposed to a high concentration of nutrients contained in the host blood. Protein synthesis during this phase probably resembles that which takes place in laboratory growth medium. Following penetration of the midgut lining, the spirochetes migrate to the hemolymph. The plasma of the hemolymph contains ions, sugars, fatty acids, amino acids and proteins. The main proteins in the hemolymph are enzymes (esterase, alkaline phosphatase), humoral defense proteins and x-globulins from the host. While nutrients are still readily available, they are at a lower concentration compared to the host blood. Eventually, the spirochetes migrate to the salivary glands from which they are delivered to the host.

The salivary glands of the tick are intricately involved in the transmission of pathogens. Kurtii, T. J., Munderloch, U. G., Hayes, S. F., Krueger, D. E., and Ahlstrand, G. A., Ultrastructural Analysis of the Invasion of Tick Cells by Lyme Disease Spirochetes (*B. burgdorferi*) In Vitro, Can J. Zool. In press, 1994. They are composed of epithelial cells that play an important role in water balance by eliminating excess water and ions during feeding and by taking up atmospheric water during nonfeeding periods. Needham, G. R. and Teel, P. D., Off-Host Physiological Exology of Ixodid Ticks, Annu,. Rev. Entomol, 36:659–681, 1991. Several factors excreted by salivary gland cells are important for successful feeding of the tick, including anti-complement and anti-inflammatory compounds and a protein that aids in attachment. The saliva itself is alkaline with a pH of 9.5 and has a protein concentration of about 50 $\mu$g/ml. It is hypertonic relative to the hemolymph for sodium and chloride and is isotonic for potassium in several Ixodid species.

The response of *B. burgdorferi* to incubation in *Ixodes scapularis* midgut extract from engorged ticks and saliva from engorged ticks by examining proteins synthesized during these incubations is set forth hereinafter. Protein synthesis in *B. burgdorferi* was also examined during incubation under starvation-like conditions. Synthesized proteins were visualized by radioactive labelling with [$^{35}$S]-methionine followed by SDS-PAGE. These were then compared to proteins synthesized during incubation in RPMI, a medium used to simulate a growth situation. A number of proteins were found to be regulated by the incubation condition, some with established identity. However, some proteins that have not yet been identified in the literature and having significant expression in the saliva were discovered, namely kDa 19, kDa 22 and kDa 24.

Saliva induction of protein synthesis could not be simulated by incubating the cells under starvation conditions, however, it was found that some proteins with decreased expression in saliva also exhibited decreased expression under starvation conditions. Furthermore, the majority of the saliva-induced proteins were found to be membrane associated, indicating a possible role of the saliva in triggering the spirochete for invasion of or attachment to tick or host cells during the transmission process.

Bacterial Strains and Growth Conditions.

Low passage *B. burgdorferi* T15, a strain of *B. burgdorferi* isolated from saliva by the presently described methods was used for all labelling studies as well as immunoblots and surface proteolysis experiments. Cells were grown in BSKII, Barbour, A. G., Isolation and Cultivation of Lyme Disease Spirochetes, Yale J. Biol. Med., 57:521–525, 1984, at 33° C. and harvested during late log phase for all experiments. The isolate T-15 is stored and available at the University of Rhode Island, Kingston, R.I.

Cultivation of *B. burgdorferi* from Saliva
  Saliva and Midgut Extract Collection.
  Adult Ixodes scapularisticks were collected by flagging at three locations during the fall of 1992. Sampling sites were located in Rhode Island (Webster, Charlestown), Massachusetts (Ipswich), and Pennsylvania (Bryn Athen). All ticks were stored in vials and were maintained at 98% humidity and 5° C. for up to 5 months before inducing salivation. To prepare ticks to salivate, they are allowed to engorge partially by feeding on the blood of one of two New Zealand white rabbits. In the first trial, 40 mating pairs of ticks from Ipswich were placed on one ear and 40 mating pairs of from Webster (Charlestown) were placed on the other ear. In the second trial, 40 mating pairs from Pennsylvania were allowed to feed on a single ear. Ticks were contained on the rabbit's ear by using cloth bags affixed with tape. Mostly replete *I. scapularis* ticks were harvested from the first rabbit on the fifth, sixth and seventh days postattachment. All ticks were harvested from the second rabbit on the sixth day postattachment. Upon harvesting, ticks were rinsed in distilled water and were then immediately fixed to glass slides with double-sided tape, and a sterile glass micropipette was placed around the hypostome to collect saliva. Salivation was induced by the application of 2 $\mu$l of pilocarpine (50 $\mu$g/ml) in 95% ethanol to the scutum of the tick. Additional 1-$\mu$l volumes of pilocarpine were applied at 20-minute intervals when little salivation was observed. Ticks were incubated at 35° C. in a humid chamber until salivation ceased (2 to 3 hours). Micropipettes were removed from the ticks, and the amount of saliva collected was determined. Typically, volumes range from 10 to 20 $\mu$l per tick. Saliva was stored at 20° C. until use. Midgut material was collected by removing it with a syringe from engorged ticks after collection of the saliva. Phosphate buffered saline was added to make the material less viscous and it was filtered through a 0.22 $\mu$M syringe filter. Prior to labelling studies, the saliva and midgut were exposed to ultraviolet light for ten minutes to ensure sterility.

Cultivation of *B. burgdorferi* from *Ixodes scapularis* Saliva.

Following collection of saliva from engorged *I. scapularis* ticks, the saliva from each tick (10–20 $\mu$l) was added to 1 ml BSKII containing kanamycin (8 $\mu$g/ml) or rifampin (50 $\mu$g/ml). The tubes were then incubated at 33° C. and observed periodically by phase microscopy for the presence of spirochetes. Tubes containing spirochetes were then subcultured in BSKII without antibiotics. After 2–3 passages, the cells were mixed in glycerol by adding 0.85 ml culture of 0.15 ml 90% glycerol and stored at −70° C.

Protein Synthesis in RPMI, Midgut and Saliva
  Radioactive Labelling.

Radioactive labelling was performed as described in Carreiro, Margaret M., Laux, D. C., Nelson, D. R., Characterization of the Heat Shock Response and Identification of Heat Shock Protein Antigens of *B. burgdorferi*, Infect. and Immun., 58:2186–2191, 1990. For labelling studies in saliva and midgut extract, late log phase cells were harvested by centrifugation (8,000×g, 10 min()) and washed twice in PBS. Approximately 5×10$^6$ cells were resuspended in 30 $\mu$l of tick saliva or midgut and 3 $\mu$l [$^{35}$S] methionine was added. This suspension was incubated in a candle jar at 33° C. for 20 h. Labelling was stopped by the addition of 5 $\mu$l of unlabelled methionine (10 mg/ml). The cells were harvested by centrifugation and washed twice in PBS. To facilitate full recovery of the labelled spirochetes, an excess amount of unlabelled heat killed cells was added to the suspension prior to washing.

1 and 2-dimensional SDS-PAGE.

Following radiolabelling, cells were prepared for either 1-dimensional SDS-PAGE, Laemmli, U. K., Cleavage of Structural Proteins During Assembly of the Head of Bacteriophase, T4, Nature, 227:680–685, 1970, or 2 dimensional electrophoresis, O'Farell, P. H., High Resolution of Two Dimensional Electrophoresis of Proteins, J. Biol. Chem. 250:4007–4021, 1975.

Sodium Dodecyl Sulfate Polyacrylamide Gel Electrophoresis (SDS-PAGE).

Gels were prepared by mixing SDS-PAGE reagents in a 250 ml flask and pouring the mixtures between two clean glass plates sealed at the sides and bottom. Gels consisted of a stacker gel layered on top of a running gel. The stacker gel was always made with 3% acrylamide and for a 0.75 mm gel consisted of the following ingredients: 3.4 ml water, 1.5 ml 5 mM Tris base (pH 6.8), 1.0 ml acrylamide, 60 µl 10% ammonium persulfate and 60 µl 10% SDS. Polymerization was initiated with 5 µl tetra-methylethylene diamine. The concentration of acrylamide in the running gel typically ranged from 10–14%. Gels were allowed 45–60 minutes to polymerize depending on the temperature. Samples for electrophoresis were solubilized in sample buffer and placed in a boiling water bath for 5 minutes. The samples were cooled to room temperature and loaded into the wells of the stacker gel. The gel was subjected to 15 mA per gel for migration of the proteins through the stacker gel and 25 mA per gel for migration through the running gel. Resolved proteins were visualized by staining typically with Coomassie Blue R250. In the case of radioactively labelled proteins, visualization was by fluorography, a process to be described later.

Reagents used for SDS-PAGE 5 mM Tris, pH 6.8: 3 g Tris-base was dissolved in 45 ml distilled water and the pH adjusted to 6.8. The volume was brought up to 50 ml with distilled water.

15 mM Tris, pH 8.8: 18 g Tris-Base was dissolved in 80 ml distilled water and the pH adjusted to 8.8. The volume was brought up to 100 ml with distilled water.

10% ammonium persulfate: 50 mg ammonium persulfate was added to 500 µl distilled water just prior to use.

10% sodium dodecyl sulfate (SDS): 10 g sodium dodecyl sulfate was dissolved in 80 ml distilled water. The volume was adjusted to 100 ml.

Acrylamide: 0.8 g Bis-acrylamide, 30.0 g acrylamide was dissolved in 70 ml distilled water. The volume was adjusted to 100 ml.

Running gel (12%): 6 ml acrylamide, 5 ml distilled water, 3.75 ml 15 mM Tris-pH 8.8, 75 µl 10% ammonium persulfate, 150 µl 10% SDS, 5 µk Tetra-ethylene-diamine (TEMED).

Stacker gel: 1 ml acrylamide, 1.5 ml 5 mM Tris-pH 6.8, 3 ml distilled water, 60 µl 10% ammonium persulfate, 60 µl 10% ammonium persulfate, 60 µl 10% SDS, 3 µl TEMED.

Stains: Coomassie blue R250. 500 mg Coomassie blue R250 was dissolved in 1 liter of a solution of 50% methanol and 10% acetic acid.

Sampler buffer: 20 ml 10% SDS, 20 ml glycerol, 15 ml 5 mM Tris (pH 6.8), 5 ml β-mercaptoethanol.

For 1-dimensional SDS-PAGE, the cells were resuspended in 50 µl sample buffer and boiled for 5 minutes. The proteins were resolved in 12% polyacrylamide gels and examined by fluorography.

Isoelectric focusing was performed according to the method of O'Farrell, supra. Isoelectric focusing gels were prepared as follows: 10 glass isoelectric focusing tubes were cleaned by soaking in a dilute solution of micro for 10 minutes and then extensively rinsed in distilled water. They were then briefly soaked in an 0.5% solution of photo-flo (Kodak) and dried in a 50° C. oven. The tubes were then placed in a 50 ml glass graduated cylinder (as many as could fit) in a vertical position. The tubes were 20 cm long, had an inner diameter of 1 mm and an outer diameter of 3 mm. Preparation of the actual isoelectric focusing gels was carried out in a 15 ml Corex tube prior to transfer to the glass tubes. The following ingredients were added to the Corex tube: 3.45 g urea, 0.8 ml Duracryl acrylamide (Gibco BRL), 1.2 ml distilled water, 1.2 ml 10% Triton X-100, pH 5–8 ampholines (0.24 ml for pH 5–7 gels, none added for pH 3–10 gels), and pH 3–10 ampholines (0.06 ml for pH 5–7 gels and 0.3 ml for pH 3–10 gels). This mixture was dissolved by mild heating and vortexing and degassed for 15 minutes in a vacuum chamber. To the solution was added 6 µl 10% ammonium persulfate and TEMED (4.2 µl for pH 5–7 gels and 8.4 µl for pH 3–10 gels). Using a glass Pasteur pipette, this solution was transferred into the graduated cylinder containing the IEF tubes. To bring the level up to a 12 cm mark in the IEF tubes, distilled water was carefully layered on top of the acrylamide solution, pushing it up through the tubes. Polymerization was carried out for 1 hour.

Sample preparation was carried out as follows: Typically $10^7$ cells (25–50 µg protein) were resuspended in 50 µl PBS to which 50 mg urea and 100 µl lysis buffer was added. The suspension immediately clarified as the cells dissolved. The sample was layered onto either a pH 5–7 or pH 3–10 Isoelectric focusing gel and overlayed with overlay buffer. The tubes were placed in the Isoelectric focusing chamber. The top chamber contained 0.8% NaOH and the bottom chamber contained 0.08% phosphoric acid. The samples were focused for 16 hr at 400V followed by 1 h at 800V (Hoeffer Scientific). Following isoelectric focusing, the tube gels were extruded by air pressure into sample buffer and stained for 15 minutes. They were then placed on top of a 1.5 mm 12% polyacrylamie gel and subjected to electrophoresis.

The gel was subjected to 15 mA per gel for migration of the proteins through the stacker gel and 25 mA per gel for migration through the running gel. The slab gels were dried and examined by fluorography.

Reagents used for isoelectric focusing gels:

pH 3–10 ampholines (Bio-Rad)

pH 5–7 ampholines (Bio-Rad)

Lysis buffer: 5.7 g urea, 2.0 ml 10% Triton X-100, 0.5 ml β-mercaptoethanol, 0.5 ml pH 5–7 ampholines, 1.4 ml water.

10% Triton X-100—1 ml of Triton X-100 was added to 9 ml water and dissolved by vortexing.

10% Ammonium persulfate—50 mg in 0.5 ml water.

Duracryl Acrylamide (Gibco BRL)—30% acrylamide, 0.8% Bisacrylamide.

Surface Proteolysis.

Surface proteolysis was performed as previously described. Wallich, R., Simon, M. M., Hofman, H., Moter, S. E., Schaible, U. E., and Kramer, M. D., Molecular and Immunological Characterization of a Novel Polymorphic Lipoprotein of *B. burgdorferi*, Infec. Immun., 61:4158–4166, 1993. Briefly, cells were harvested by centrifugation and resuspended in 400 µl PBS at $10^8$ cells/ml. Half of the sample was treated with proteinase K (0.5 mg/ml) and the other half left untreated. Alternatively, [$^{35}$S]methionine labeled cells were mixed with unlabelled cells followed by treatment with proteinase K. All samples were then incubated for 1 hour at 25° C. Labelling was stopped by the addition of PMSF and the proteins examined by SDS-PAGE and fluorography.

Immunoblots

Western Blot Analysis.

To confirm the identity of the proteins purified by 2-dimensional electrophoresis, proteins from *B. burgdorferi* T15 were separated by isoelectric focusing and PAGE and transferred to nitrocellulose membranes (BIO RAD) (Towbin). The membranes were blocked by immersion in TBS—2% Tween 20 for 10 minutes. Following a washing step in TBS (5 min), membrane sheets were immersed in primary antibody diluted 1:1000 in TBS()—0.05% Tween 20 and incubated with shaking for 1 hour. After 2 five minute washing steps in TBS, the sheets were immersed in Horse radish peroxidase conjugated anti-mouse monoclonal antibody diluted 1:2000 and allowed to incubate 45 minutes with shaking. Reactive proteins were visualized with 3,3,5,5 Tetramethyl benzidine and dioctyl sulfo-succinate mixed with 0.025% hydrogen peroxide.

Examination of Protein Synthesis Under Various Nutritional Conditions

Starvation Labelling of B. Burgdorferi.

B. burgdorferi was labelled as above in solutions containing various amounts of nutrients. To a Balanced Balts Solution (Gibco, BRL, Gaithersburg, Md.) was added varying amounts of either BSA or glucose. The solution was then adjusted by pH 7.3. When the glucose level was held constant (0.1%), the amount of BSA was varied by the following amounts: 1, 10, 25, 50, 100, 500 μg/ml. When the amount of BSA was held constant (50 μg/ml), the amount of glucose was varied by the following amounts: 0.001, 0.005, 0.01, 0.05, and, 0.10% B. burgdorferi was then labelled in 100 μl of each labelling condition for 20 hours in a candle jar. The labellings were done in parallel with radioactive labelling in saliva.

Reagents Used for Starvation Labelling Experiments:
Balanced Salts Solution (BSS) (mg/liter) $CaNO_3$ (100), KCl(400), $MgSO_4$ (48.84), NaCl(6000), $NaHCO_3$(2000), $Na_2HPO_4$(800)

Heat Denaturation and Glucose Addition.

The effects of glucose addition and heat treatment were examined. Tick saliva was divided into three portions of equal volumes. One portion was subjected to 100° C. for 10 minutes to denature protein. To another portion was added glucose to 0.1%. The third portion was the control and was not treated. B. burgdorferi was suspended in the treated saliva and labelled with [$^{35}$S]methionine as described above.

Subcellular Localization of Saliva Induced Proteins

Subcellular Fractionation of Saliva Induced Proteins.

B. burgdorferi was radioactively labelled with [$^{35}$S] methionine in tick saliva. Following labelling the cells were mixed with an excess of unlabelled heat-killed cells and fractioned into soluble and membrane fractions. The membrane fraction was then separated into Triton X-100 soluble and insoluble proteins. Following fractionation, the proteins were resolved by SDS-PAGE and visualized by fluorography as described above.

Discussion

Isolation of B. burgdorferi from Ixodes scapularis Saliva.

To strengthen the hypothesis that B. burgdorferi is transmitted to a host via the tick's saliva, BSKII was inoculated directly with saliva from I. scapularis ticks collected at various geographical locations. Following inoculations of saliva into BSKII and incubation at 33° C., spirochetes were detected in some samples by as early as 3 days.

TABLE 1

B. burgdorferi isolated from I. scapularis saliva

| Isolate number | Days after: Tick attachment that saliva was collected | Inoculated spirochetes were detected in culture |
| --- | --- | --- |
| I4 | 5 | 3 |
| P1 | 6 | 6 |
| I2 | 8 | 8 |
| W2 | 5 | 8 |
| I11 | 6 | 14 |
| P2 | 6 | 20 |
| I3 | 5 | 21 |
| W7 | 6 | 21 |
| I18 | 5 | 25 |

At 6 days, the first visible pellet appeared in the culture tube containing saliva from tick 14 (Ipswich, tick number 4) at which time the cells were subcultured. The last sample to be subcultured (I18) was at 25 days after inoculation. In all cases in which saliva-inoculated medium produced B. burgdorferi, the cells grew in large clumps at the bottom of culture tubes. However, after subculturing for 5 to 6 weeks, B. burgdorferi cells were observed growing at a high density throughout the culture, similar to the growth of highly passaged strain B31.

Protein profiles of whole-cell lysates from salivary isolates I1, I3, and W7 (Webster) were examined by SDS-PAGE and were compared with the high-passage strain, B31. Cells were grown in 5 ml BSKII and washed in RPMI. The washed cell pellets were resuspended in 100 μl of RPMI and broken by 10 seconds of continuous sonication. Protein concentrations were measured by the assay of Bradford, M., Anal. Biochem., 72:248 (1976). Equal amounts of proteins were then resolved by SDS-PAGE on a 12% polyacrylamide gel. Coomassie blue and silver stainings of whole-cell protein lysates showed lower a mounts of surface proteins OspA and OspB in strain B31 compared with the amounts in the salivary isolates. Previous reports indicate that OspB is lost during passage of B. burgdorferi. Isolate W7 had two proteins with molecular masses of approximately 50 and 44 kDa that were not present in the other isolates examined or in strain B31. Isolates I2 and I3 each had a protein band at 30 kDa that was not present in B31 or isolate W7. Conversely, a 22 kDa protein was detected in B31 but was not found in any of the salivary isolates. This result is consistent with that of previous work, Schwan, T. G., W. Burgdorfer and C. F. Garon, Changes in Infectivity and Plasmid Profile of the Lyme Disease Spirochete, B. burgdorferi, as a Result of In Vitro Cultivation, Infect. Immun. 56:1831–1836, 1988, which demonstrated a relative increase in a lower molecular weight protein with continued laboratory culture of B. burgdorferi. FIG. 1A illustrates a coomassie blue stain of the salivary isolates and B-31.

Figure 1B:
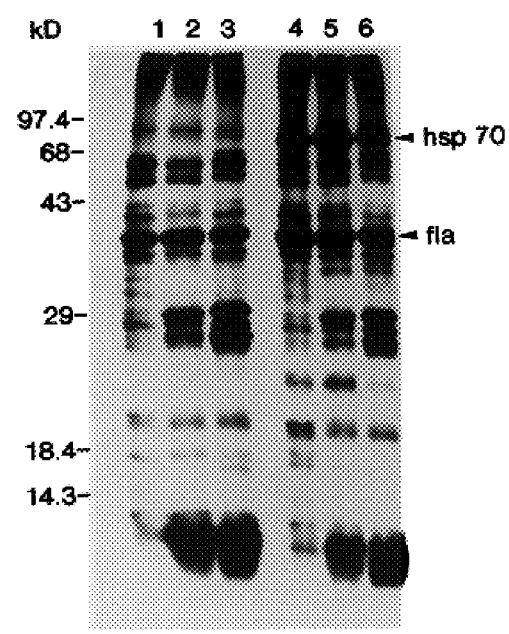

The protein profiles of two salivary isolates, I4 and W2, labelled with [$^{35}$S] methionine were examined by SDS-PAGE and fluorography and were compared with that of B31. Cells grown in BSKII medium (30 ml) were washed three times in RPMI without methionine and were resuspended in 400 μl RPMI without methionine. The cells were then labelled with 10 μCi of [$^{35}$S]methionine (specific activity, 800 Ci/mmol) for 1 hour at 33° C. Examination of the labelled protein profiles showed few differences except in the low molecular weight region. OspA and a protein of about 25 kDa were present in reduced amounts or were absent from B31. Additionally, isolates I4 and W2 each exhibited a large band at approximately 8 kDa which was not detected in B31. It is interesting that this band was not apparent in any strain in coomassie blue or silver stained gels. FIG. 1B shows the labelling patterns of the salivary isolates and B-31.

SDS-PAGE Analysis of Saliva Regulated Proteins.

Figure 3A:
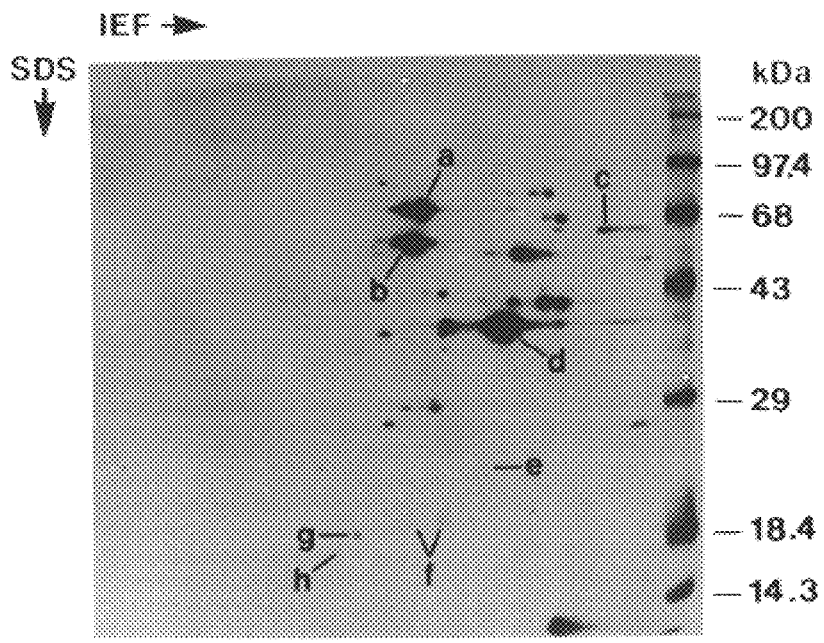
Figure 3B:
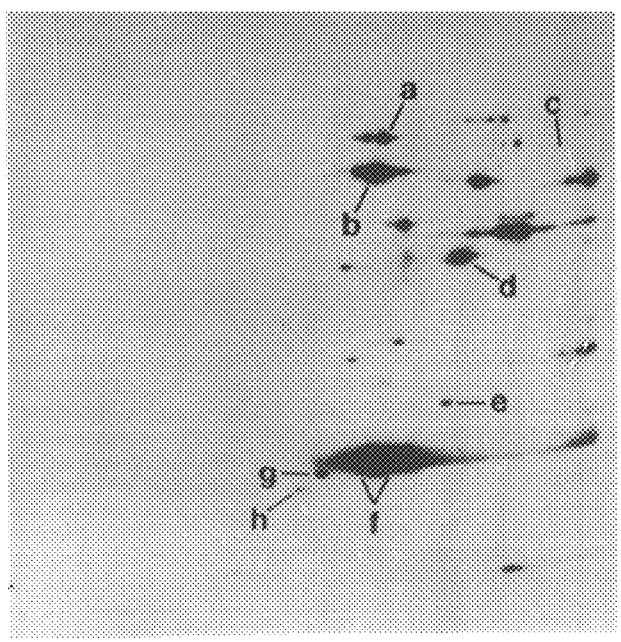
Figure 4A:
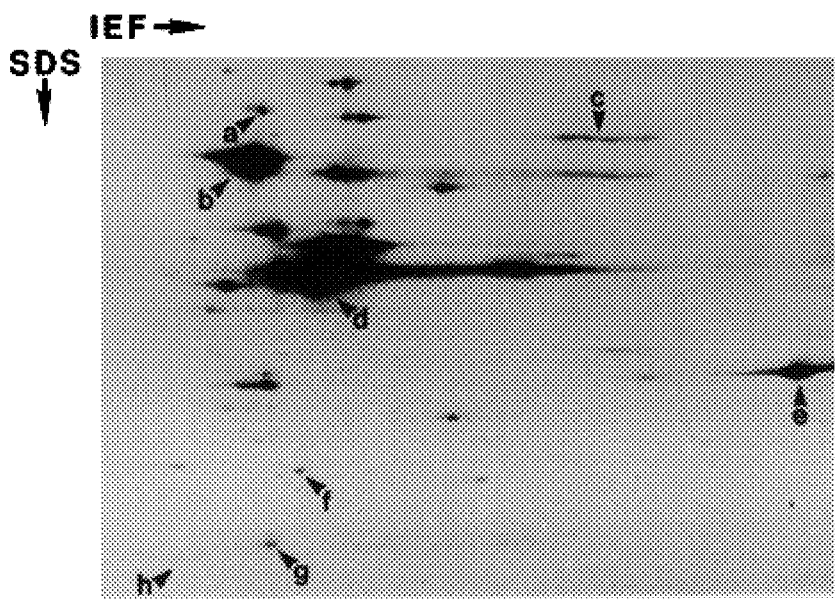
Figure 4B:
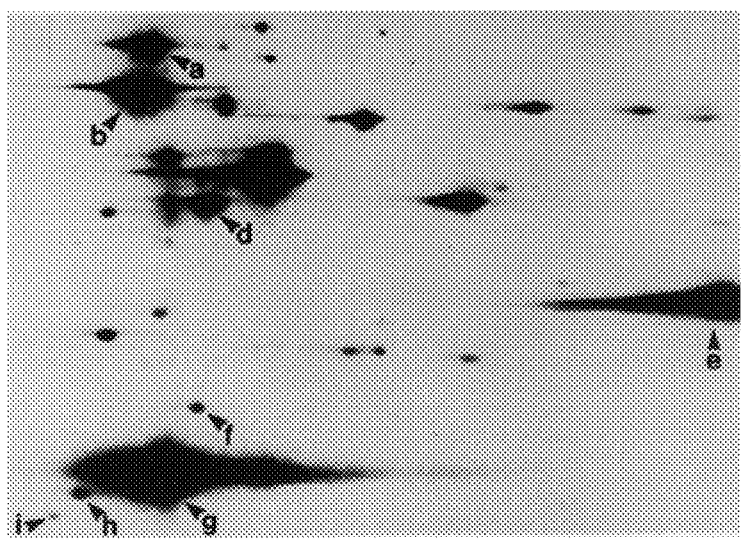
Figure 4C:
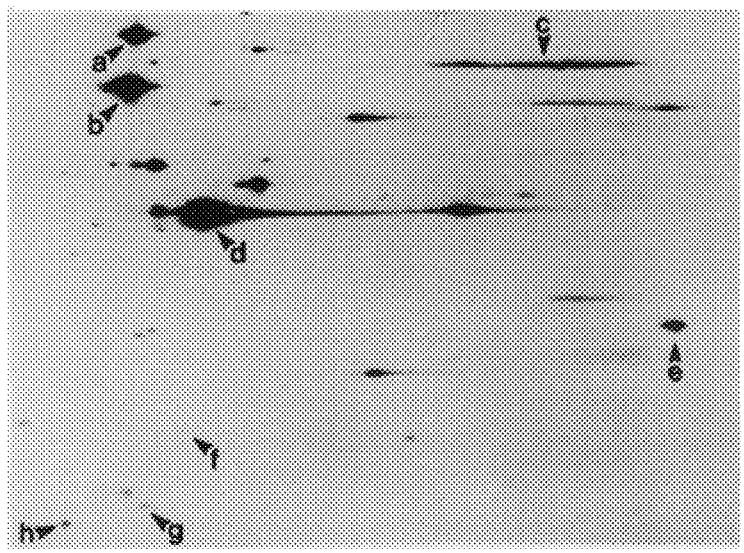

To investigate the effect of exposure of B. burgdorferi tick saliva, low passage (<5 passages) cells were harvested from growth media and washed in PBS followed by incubation in saliva with [$^{35}$S]methionine for 20 hours as described in Materials and Methods. Proteins synthesized during incubation in saliva were compared with those synthesized in tick midgut and in RPMI by 1- and 2-dimensional SDS-PAGE followed by fluorography. Relatively few differences were detected in protein profiles of cells labelled in RPMI compared to tick midgut. However, analysis of cells, labelled in I. scapularis saliva revealed several proteins with significantly altered expression. At least 8 proteins were found to be regulated by exposure to tick saliva as determined by SDS-PAGE and fluorography. Proteins with molecular weights of 19, 22, 24, 31, and 34 kDa exhibited greater intensity while proteins of 41 and 66 kDa had reduced intensity compared to cells labelled in RPMI and midgut. A 70 kDa protein exhibited greater intensity in cells labelled in saliva compared to RPMI, but was not greater than cells labelled in midgut extract. The differences in relative intensities of these proteins occasionally showed some variation between experiments, in particular, the intensities of the 22 and 24 kDa proteins. This may be due to slight differences in composition of the various batches of saliva collected. Overall, however, the results were consistent. FIGS. 3 and 4 illustrate the protein profiles of cells radioactively labelled in RPMI, tick midgut or tick saliva and resolved by 2-dimensional electrophoresis. Labelled proteins were isoelectrically focused in either pH 5–7 gels (FIGS. 3A,B) or pH 3–10 gels (FIGS. 4A,B,C). The pH 5–7 gels allowed resolution of 2 bands close together at 22 kDa. The more acidic of the two proteins appears to be the one highly induced in saliva. In the pH 3–10 gels, only one was visible.

In order for a protein to be visualized by isoelectric focusing, it must be in the pH range of the isoelectric focusing gel. The 31 and the 34 kDa proteins were not visible in the pH 5–7 gels and were only occasionally visible at the basic end of the pH 3–10 gels. The molecular weights of these proteins and their high isoelectric points suggested that they may correspond to outer surface proteins A and B. This was confirmed by immunoblot analysis (see below and FIG. 2).

To ensure that the observed results in long term labelling (20 hours) were reflective of labelling during initial exposure to saliva or midgut, cells were suspended in saliva or midgut as described above. At various time intervals, a portion of the cells was removed and pulsed for 3 hours in either saliva or midgut (0, 3 and 17 hours). The labelled proteins were resolved by SDS-PAGE and visualized by fluorography. The profiles of the early labelling (0, 3 hours) were consistent with those of the longer labelling (17 hours). This suggests that the long labelling period required to obtain enough labelled protein for 2-dimensional SDS-PAGE analysis is an accurate reflection of protein synthesis during initial exposure. Longer labelling periods were necessary, however, to obtain enough incorporation for 2-dimensional electrophoresis analysis.

Immunoblot Analysis.

In order to determine the exact identity of the proteins exhibiting marked increased or decreased expression during incubation in saliva, 1 and 2-D immunoblots were performed with a variety of antibodies. Proteins from *B. burgdorferi* were separated by either 1- or 2-dimensional gel electrophoresis, transferred to nitrocellulose membrane and probed with mon-specific antibodies against OspA (H5332), OspB (H6831), Hsp70 (LA3), Hsp60 (LA8), and the recently identified lipoprotien, pLA7 (LA7) (60). For 2-dimensional immunoblots, proteins were resolved in the fist dimension by isoelectric focusing in pH 3–10 gels (FIG. 2). For purposes of more effective comparison between probed proteins and saliva-induced proteins, the 2-D immunoblots were performed with proteins from radioactively labelled cells. Following immunoblotting, the nitrocellulose was dried and used to expose an autoradiography plate. Following exposure of the X-ray plate, the autoradiograph was superimposed on the probed nitrocellulose. This made it possible to determine which labelled proteins corresponded to the proteins probed for in the immunoblot.

Figure 2A:
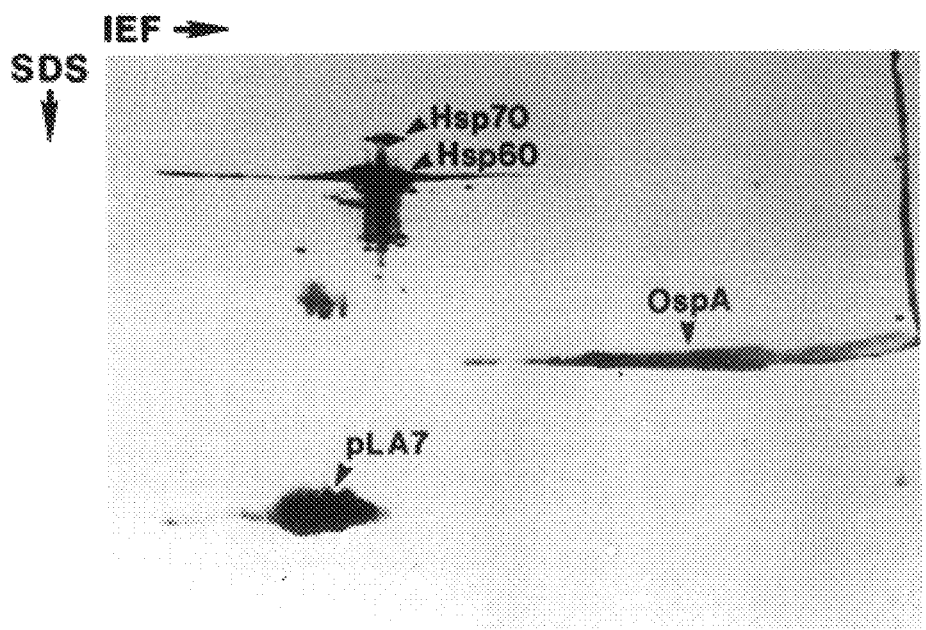
Figure 2B:
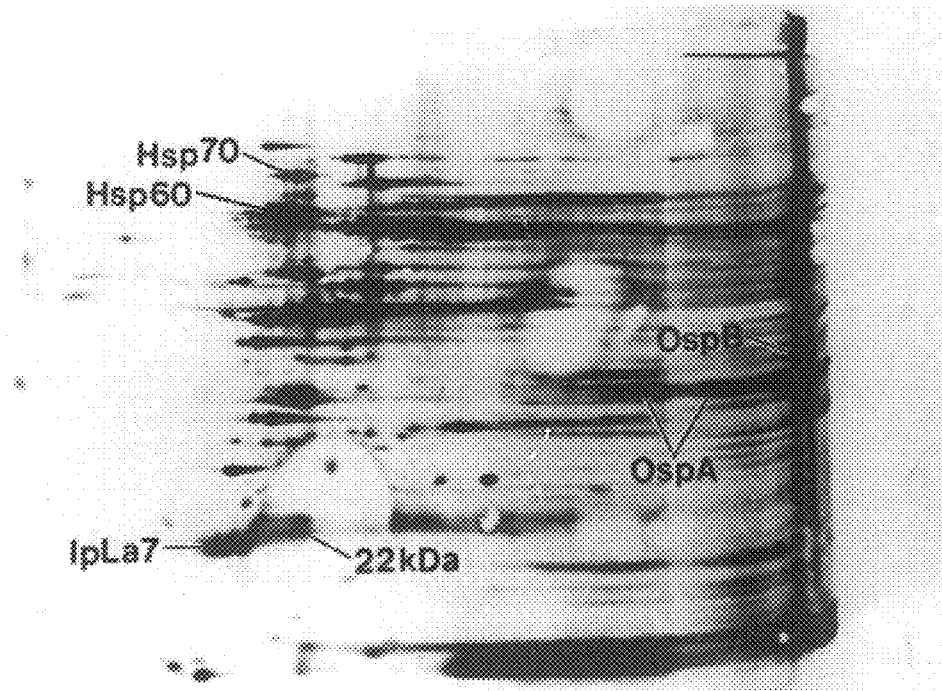

From these experiments it was determined that the 31 and 34 kDa proteins corresponded to OspA and OspB, respectively, and that the 70 kDa protein corresponded to Hsp70. FIG. 2 illustrates the probed proteins (FIG. 2A and the resulting autoradiogram (FIG. 2B) from the immunoblot. Antibody LA7 was used because of similarities between the highly saliva-induced 22 kDa protein and pLA7. The molecular weight and isoelectric point of pLA7 are reported to be 5.9 and 21.9 kDa respectively, and the isoelectric point of the 22 kDa protein as calculated from the 2-D autoradiogram was found to be 6.0. This protein was not recognized by LA7 and consistently ran slightly basic to pLA7 during isoelectric focusing. These data suggest that this is as yet an unidentified protein that appears to be strongly induced during incubation in *I. scapularis* saliva.

Quantification of Saliva-induced Proteins.

Figure 5:
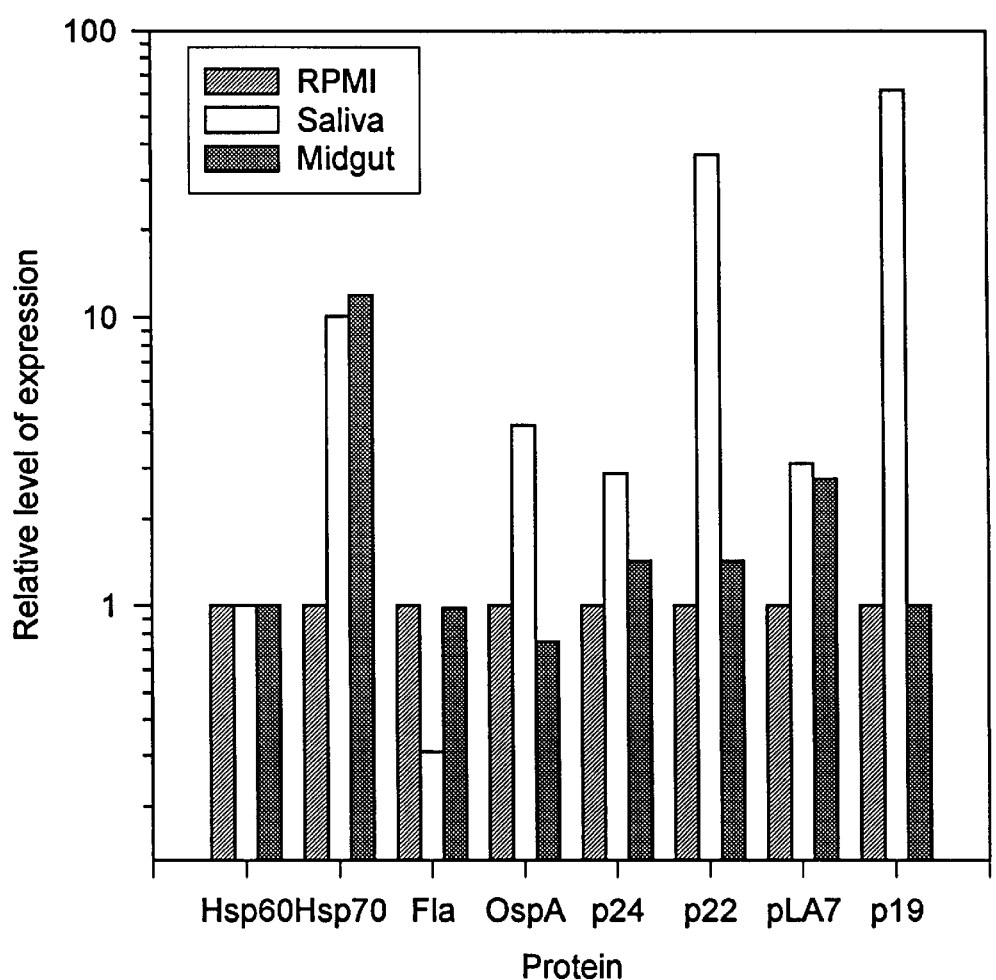
Figure 6A:
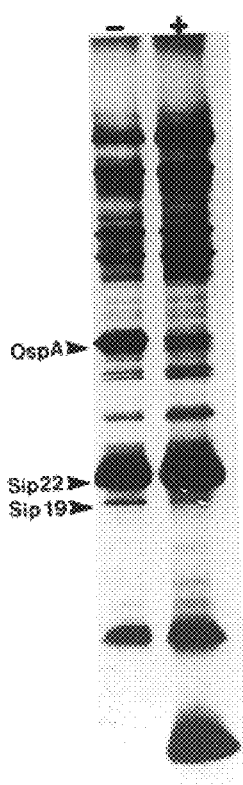
Figure 6B:
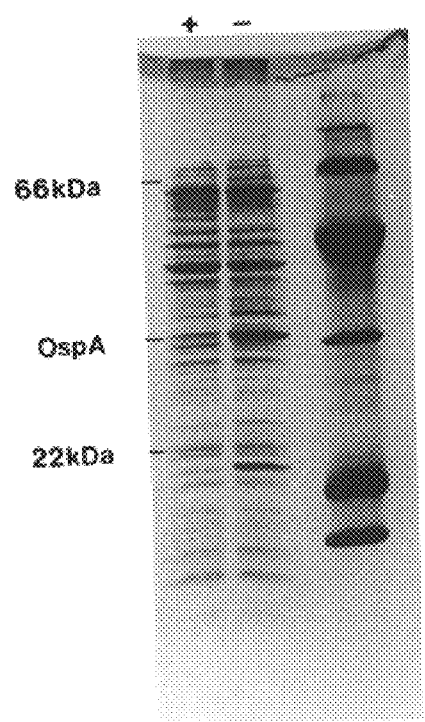
Figure 7:
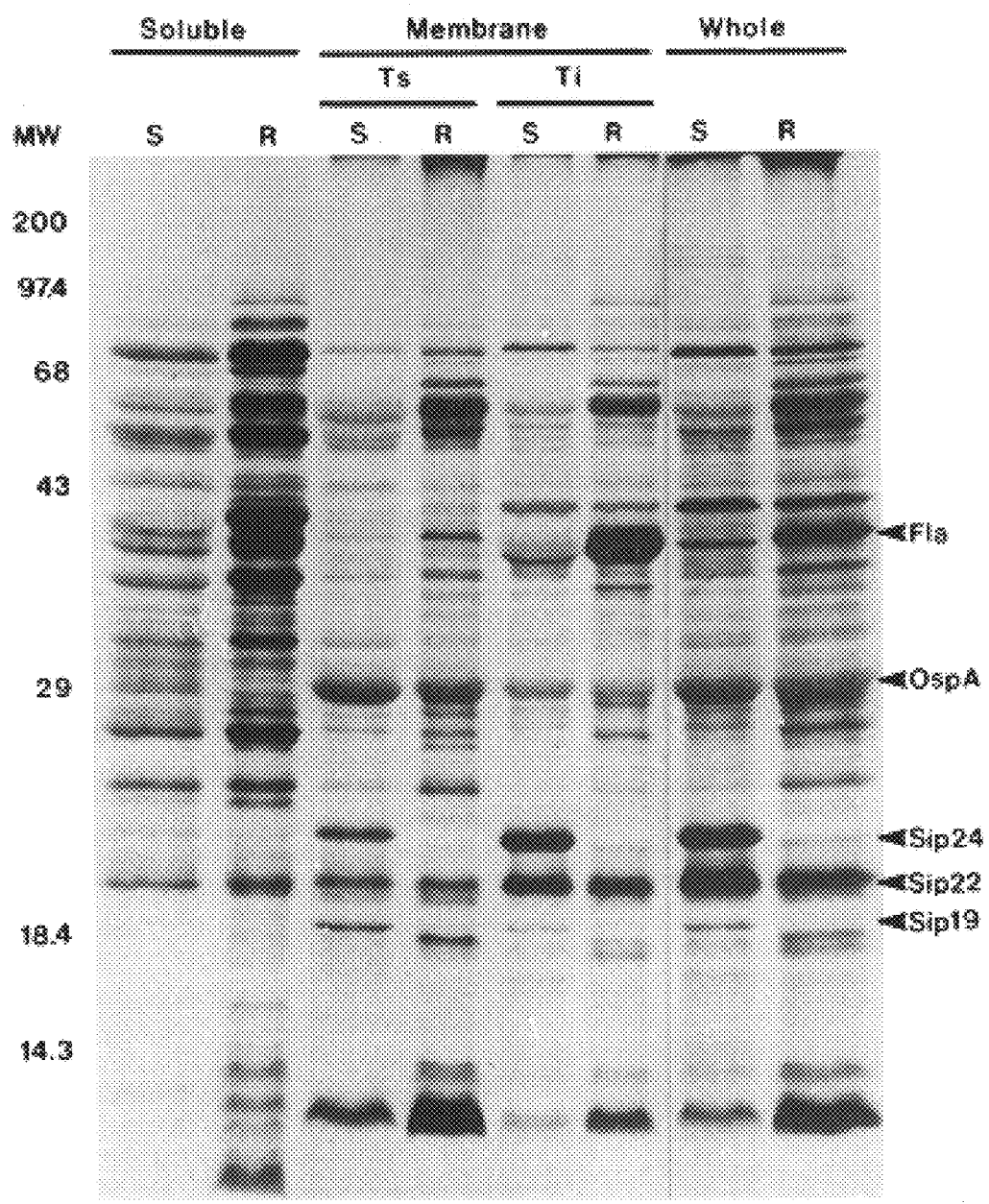

The relative amounts of proteins synthesized during incubation in *I. scapularis* saliva, midgut, or RPMI were determined by image analysis of autoradiograms and are listed in Table 2 below and illustrated in FIG. 5.

TABLE 2

Relative levels of expression of selected proteins in *B. burgdorferi* cells incubated in RPMI, *I. scapularis* saliva or *I. scapularis* midgut extract

| Protein | RPMI | *I. scapularis* saliva (change rel. RPMI) | *I. scapularis* midgut extract (Change rel. RPMI) |
|---|---|---|---|
| Hap60 | 1.000 | 1.000 (1.00) | 1.000 (1.00) |
| Hsp70 | 0.041 | 0.515 (12.56) | 0.492 (12.00) |
| p66 | 0.190 | 0.006 (0.03) | 1.143 (6.02) |
| Flagellin | 1.565 | 0.346 (0.22) | 1.555 (0.99) |
| OspA | 0.353 | 1.602 (4.54) | 0.263 (0.75) |
| p24 | 0.033 | 0.083 (2.52) | 0.053 (1.61) |
| p22 | 0.057 | 3.258 (57.16) | 0.126 (2.21) |
| pLA7 | 0.00 | 0.070 (>70) | 0.105 (>100) |
| p19 | 0.00 | 0.040 (>40) | 0.00 (nc) |

The intensity of the OspA band from cells labelled in saliva is approximately 4.5 times higher than cells labelled in RPMI and 6.1 times higher than in cells labelled in midgut extract. Similarly, the intensity the OspB band is 1.5 and 2.1 times higher, respectively. The values for OspA band intensity were taken from 1-dimensional gels. Because of its high pH (9.7), it did not migrate into the isoelectric focusing tube and was generally not visible in the 2-dimensional autoradiograms. Both OspA and OspB have been implicated in various reports to be associated with attachment and infectivity properties of *B. burgdorferi*. The results from the labelling experiments thus suggest that *I. scapularis* saliva may trigger the spirochete for entry into the host by inducing increased synthesis of these outer surface proteins. As these are reported important factors for virulence, such a response by the spirochete would probably increase its invasive capabilities in vivo.

The only other protein with known identity that was labelled at significantly higher levels during incubation in saliva was the heat shock protein, Hsp70. The band corresponding to Hsp70 was 12.5 times higher than in RPMI and midgut labelled cells, respectively. Synthesis of Hsp70 has been shown to be regulated by a variety of factors in prokaryotic and eukaryotic cells. These factors include heat shock, starvation, exposure to acid, and oxidative stress. The relative paucity of nutrients in saliva (the protein concentration is approximately 50 µg/ml) compared to growth medium suggested that Hsp70 induction may be a starvation response. However, levels of newly synthesized Hsp70 in *B. burgdorferi* cells incubated in midgut extract were also elevated (FIG. 4). Induction of Hsp70 synthesis during labelling may thus be due to some other factor. Labelling of

*B. burgdorferi* in RPMI in which the volume of resuspended cells was equal to that used for saliva incubation resulted in large amounts of Hsp70 synthesized. When the volume of RPMI was high (0.5 ml) and the labelling time was minimal (1 h), little Hsp70 was synthesized.

*B. burgdorferi* cells experience an increase in environmental temperature of approximately 10–15° C. during the transition from midgut to hose. It has previously demonstrated that elevated temperatures dramatically induce synthesis of Hsp70 in *B. burgdorferi*. Induction of Hsp70 synthesis during incubation in saliva may aid in successful adaptation to the increased environmental temperature experienced by the spirochete.

Newly Identified Proteins

Other proteins synthesized at relatively higher levels in saliva were also quantified. The intensity of the 22 kDa protein was consistently elevated in saliva-incubated cells, being up to 57 times that in RPMI and 25 times that in midgut labelled cells. Its intensity varied for different experiments but was always significantly higher in saliva incubated cells compared to cells labelled in RPMI or midgut. The 19 kDa protein was an acidic protein with a pI of 5.7 as calculated from the 2-D autoradiogram. It was not visible in autoradiograms from cells labelled in RPMI or midgut extract. A 24 kDa protein was also synthesized in higher amounts in saliva. It was expressed at levels 2.5 and 1.6 times higher in saliva compared to RPMI and midgut, respectively.

While a few proteins appeared to be synthesized in reduced amounts in saliva, the 41 kDa protein corresponding to flagellin exhibited the most drastic decrease in intensity being 4.5 times less intense than the corresponding band from cells labelled in both RPMI and midgut. The same effect was observed when radioactively labelling cells under conditions of low amino acid and protein concentration.

Starvation Labelling.

In order to determine whether the response of *B. burgdorferi* to exposure to tick saliva was due to starvation, cells were radioactively labelled in starvation solutions described in Material and Methods. When cells were labelled in varying concentrations of BSA without glucose, the total amount of protein synthesized decreased with decreasing BSA concentration. The only protein that appeared to show a relative increase in synthesis with a corresponding decrease in BSA concentration was OspA. The relative levels of flagellin and a 45 kDa protein synthesis decreased with lower concentrations of BSA in the absence of glucose, however, the total amount synthesized for each protein concentration was still significantly lower than in RPMI where the amino acid nd glucose concentrations high. These results could only be observed when no glucose was present in the labelling medium. In the presence of 0.1% glucose, all samples demonstrated the same levels of protein synthesis and had nearly identical protein profiles. Similarly, with varying amounts of glucose in constant BSA concentration, the protein profiles of *B. burgdorferi* were identical.

Effects of EDTA, Glucose Addition, And Heat Denaturation.

Protein synthesis in a number of organisms has been shown to be regulated by the concentrations of certain ions. For example, low calcium concentration induces synthesis of virulence factors in *Yersinia pestis*, Mulder, B., T. Michiels, M. Simonet, M. P. Sory, and G. Cornelis, Identification of Additional Virulence Determinants on the pYV Plasmid of Yersinia Entercolitica W227, Infect. Immun. 57:2534–2541, 1989. To investigate this possibility as a mechanism of protein expression regulation by saliva on *B. burgdorferi*, cells were grown at 33° C. in the presence of EDTA at various concentrations (1, 10, 20 mM) and the proteins examined by SDS-PAGE. This treatment did not significantly affect the protein profile of *B. burgdorferi* as determined by comparison to cells grown in BSKII without EDTA. As such, it does not appear that the divalent ion concentration had a significant effect on protein synthesis in *B. burgdorferi*.

Addition of glucose to saliva, however, appeared to slightly decrease synthesis of the 24 kDa protein during radioactive labelling but did not affect the 22 kDa protein. Similarly, in cells labelled in large volumes of RPMI (0.5 ml) for short periods (1 h), the 24 kDa protein was not expressed as highly as in cells labelled in low volumes of RPMI (0.05 ml) for longer periods (20 h). Thus, the depletion of glucose from the medium may result in increased synthesis of the 24 kDa protein. While the synthesis of flagellin was increased slightly with added glucose, it was still significantly lower than in RPMI. The major difference between RPMI and saliva is the concentration of amino acids. Thus, it may be that amino acid concentration is a major factor in regulation of flagellin synthesis. The total amount of protein synthesis during incubation in saliva was dramatically increased by added glucose, being 5–10 times higher than without glucose added. These results were similar to those obtained during the starvation labelling experiments.

To investigate the possibility of regulation by an external signal in which a protein in the saliva binds to the spirochete to induce increased expression of one or more proteins, saliva was subjected to 100° C. for 10 minutes prior to radioactive labelling to denature proteins. This did not affect protein synthesis of any proteins in *B. burgdorferi* compared to the control sample.

Subcellular Localization of Saliva-induced Proteins.

The effect of exposure to *I. scapularis* saliva on synthesis of surface proteins was also investigated. These were identified by proteinase K surface proteolysis and subcellular fractionation of saliva incubated cells followed by SDS-PAGE and fluorography as described in Materials and Methods. By staining with Coomassie blue prior to fluorography, it was possible to relate a protein from the fluorogram with its corresponding-band in the coomassie stain. The fluorogram showed that OspA and OspB, a 24 kDa protein and a 19 kDa protein exhibited decreased intensity in the presence of protease (FIG. 6A). All these proteins were expressed at higher levels following incubation in saliva compared to RPMI and midgut extract. Surface proteolysis was also examined in coomassie blue stained gels of whole cell lystates (FIG. 6B). The major proteins accessible to the action of protease were the 66 kDa, OspA, OspB, and the 24 kDa protein. The 19 kDa band was not visible in Coomassie blue stained gels. This protein appears to be a surface localized protein expressed only in saliva incubated cells.

Saliva induced proteins were also examined by subcellular fractionation of cells labelled in saliva and RPMI. The majority of saliva induced proteins were found in the membrane fraction of cell lysates. The 19, 22, and 24 kDa proteins were all in the membrane fraction with the 22 and 24 kDa proteins localized primarily in the Triton X-100 soluble fraction (FIG. 7).

*I. scapularis* saliva affects protein synthesis in *B. burgdorferi* by up-regulating a number of proteins while inhibiting synthesis of others. It is believed that this may be a mechanism that serves to prepare *B. burgdorferi* for transmission from its vector into a host. At least three of the proteins whose synthesis appears to increase during incubation in saliva are membrane bound and two appear to be susceptible to the action of protease. The synthesis of membrane proteins may be important for adhesion to tick or host cells during the transmission process. Adhesion of *B. burgdorferi* to tick cells correlates with infectivity and viability and apparently requires translation of new proteins either by the host cell or the spirochete, or both, as determined by its sensitivity to puromycin, a protein synthesis inhibitor. Monoclonal antibodies to OspA and OspB do not interfere with adherence to a tick cell line, but outer membrane proteins appear to be involved because trypsinization reduces adherence of the spirochetes to the tick cells. It is possible that one or more of the membrane bound proteins highly synthesized during incubation in saliva may be important in this or other related processes. The 24 kDa protein appears to be regulated by the presence of glucose as its synthesis is decreased during incubation in saliva which contains 0.1% glucose. Therefore, environments with low glucose concentrations, such as the intracellular cytosol of host cells may induce synthesis of this protein. The amount of the 22 kDa protein synthesized by *B. burgdorferi* varied for different experiments, both during incubation in saliva and RPMI but was always higher in saliva-incubated cells. Although the cells were harvested at about the same density for each labelling experiment ($1\times10^7$ cells/ml), it is possible that minor fluctuations in the growth stage of the cells had an impact on the type and amount of proteins synthesized during the labelling process.

The change in flagellin synthesis in response to low nutrient conditions makes physiological sense when considering that flagellin represents a large portion of the total protein in *B. burgdorferi*. Conditions of low nutrient availability or non-growth such as in the tick gut prior to feeding would arrest synthesis of this protein to conserve energy. Exposure to conditions where nutrients are readily available as in the tick during feeding and subsequently in the host would result in increased synthesis of flagellin. During these processes, motility of the spirochete is vital for survival.

The effect of saliva on *B. burgdorferi* protein synthesis may be more dramatic than that specifically identified in this disclosure. The labelling conditions necessitated using at least $10^6$ cells during the labelling period to obtain enough newly synthesized protein to visualize by fluorography. The actual number of cells delivered to the host during transmission is probably between $10^2$ and $10^4$. Thus, these conditions exceed the natural concentration of cells in saliva by up to 10,000 fold. Invivo where the amount of saliva per spirochete is not limiting, the effect on protein synthesis in each cell may be relatively more pronounced. Depending on the length of time spent in the saliva, the proteins synthesized during this time may confer a significant increase in invasiveness or adaptability that results in more successful transmission and pathogenesis. The saliva may also serve to amplify these inducible proteins in *B. burgdorferi* during cycling to and from *I. scapularis* ticks which may result in a protein profile significantly different than that observed in laboratory grown cells. For example, the 19 and 22 kDa proteins are synthesized in amounts higher in *I. scapularis* saliva than in RPMI or midgut. If upon entry into a host, synthesis of these protein decreases, the relative number of copies of each protein per spirochete will decrease by an amount inversely proportional to its half-life and proportional to the number of cell divisions during incubation in the host. However, repeated cycling of this process will result in a progressively higher number of copies of the protein per spirochete until eventually an equilibrium is established. Thus, the quantity of the saliva inducible proteins may be significantly higher in spirochetes multiplying in their natural environment than in laboratory medium.

These concepts suggest a variety of experiments to determine the precise effect of salivary incubation on *B. burgdorferi*. One could easily test the attachment capabilities of the spirochete prior to and after incubation in saliva with a suitable tissue culture cell line. Simply by mixing the spirochetes with the host cells or tick cells and observing by microscopy, the ability to attach could be quantified. One could also use radioactively labelled spirochetes and allow them to attach to the host cells. Centrifugation of the host cells followed by measuring radioactivity in the cell pellet would provide a way to quantify the attachment process. Although it is possible that a single incubation in the saliva could afford the spirochete a substantial increase in its ability to attach to or penetrate the host cells, it may require multiple cycles of salivary incubation and growth to observe a significant change in physical capabilities. The actual amount of protein synthesized during migration through the salivary glands is unknown. The spirochetes take up about 1% of the [$^{35}$S]methionine during the labelling period in most labelling experiments. This translates into a relatively small amount of total protein synthesized compared to that already present in the cells. The cycle of growth and saliva exposure could conceivably be simulated by incubating the cells in saliva, harvesting them and allowing them to grow in BSKII for a few divisions. After repeating this cycle a number of times, the whole cell protein profile of the spirochetes could be examined as well as the attachment capabilities.

The foregoing description has been limited to a specific embodiment of the invention. It will be apparent, however, that variations and modifications can be made to the invention, with the attainment of some or all of the advantages of the invention. Therefore, it is the object of the appended claims to cover all such variations and modifications as come within the true spirit and scope of the invention.

What is claimed is:

1. A method for identifying proteins expressed by vector-borne pathogens transmitted to animals via saliva of blood sucking arthropods which comprises:

a) collecting the saliva from said arthropods;

b) culturing the pathogens from the saliva in a growth medium;

c) visualizing the presence of the pathogens as cells;

d) labeling and incubating the cells in a medium consisting essentially of the saliva;

e) resolving the proteins of the labeled cells;

f) visualizing the resolved proteins; and g) identifying the resolved proteins.

2. The method of claim 1 wherein the pathogens are bacterial pathogens selected from the families consisting of Borreliae, Rickettsiae, and Ehrlichiae and wherein the arthropod is selected from the family Ixodidae.

3. The method of claim 2 wherein the arthropod is *I. scapularis* and the bacterial pathogen is *B. burgdorferi.*

4. The method of claim 1 wherein the pathogen is any protozoan parasite.

5. The method of claim 4 wherein the protozoan parasite is a piroplasm.

6. The method of claim 5 wherein the piroplasm is selected from the group consisting of Babesia and Theileria.

7. The method of claim 2 which comprises:

radioactive labeling of the cells.

8. The method of claim 2 which comprises:

visualizing and identifying by one dimensional SDS-PAGE.

9. The method of claim 2 which comprises:

visualizing and identifying by two dimensional SDS-PAGE.

* * * * *